(12) United States Patent
Teoule et al.

(10) Patent No.: US 6,187,914 B1
(45) Date of Patent: Feb. 13, 2001

(54) NUCLEOSIDE DERIVATIVES, AND THEIR USE IN OLIGONUCLEOTIDE SYNTHESIS

(75) Inventors: Robert Teoule, Grenoble; André Roget, Saint Egreve; Thierry Livache, Haute Jarrie, all of (FR)

(73) Assignee: Cis Bio International, Saclay (FR)

( * ) Notice: Under 35 U.S.C. 154(b), the term of this patent shall be extended for 0 days.

(21) Appl. No.: 09/147,198

(22) PCT Filed: Apr. 30, 1997

(86) PCT No.: PCT/FR97/00770

§ 371 Date: Dec. 3, 1998

§ 102(e) Date: Dec. 3, 1998

(87) PCT Pub. No.: WO97/42207

PCT Pub. Date: Nov. 13, 1997

(30) Foreign Application Priority Data

May 3, 1998 (FR) .................................................. 96 05553

(51) Int. Cl.[7] .......................... C07H 21/00; C07H 21/02; C07H 21/04; C07H 19/167; C25B 3/00
(52) U.S. Cl. .................. 536/25.3; 536/25.31; 536/25.33; 536/25.34; 536/25.54; 536/28.54; 536/28.51; 536/27.62; 536/27.81; 536/26.7; 536/26.8; 536/27.6; 544/243; 544/244; 205/427
(58) Field of Search .............................. 205/427; 544/243, 544/244; 536/25.3, 25.31, 25.33, 25.34, 28.54, 28.51, 27.62, 27.81, 26.7, 26.8, 27.6

(56) References Cited

U.S. PATENT DOCUMENTS 5,179,200 * 1/1993 Molko et al. ........................ 536/26.8

5,837,859 * 11/1998 Teoule et al. ........................ 536/25.3

FOREIGN PATENT DOCUMENTS

94/22889 * 10/1994 (WO) .

OTHER PUBLICATIONS

De Voss et al., "General Approach to the Synthesis of Specifically Deuterium–Labeled Nucleosides", J. Org. Chem., vol. 59, pp. 2715–2723, Oct. 1994.*

Baker et al., "Irreversible Enzyme Inhibitors. 195. Inhibitors of Thymidine Kinase from Walker 256 Carcinoma Derived from Thymidine 5'–Acetate", J. of Med. Chem., vol. 15, No. 9, pp. 940–944, 1972 No Month Available.*

Shimokawa et al., "Studies on Nucleosides and Nucleotides. V. Selective Acroylation of 5'–Hydroxyl Group of Uridine and Adenosine", Bull.of the Chem. Soc. of Japan, vol. 49, No. 11, pp. 3357–3358, 1976 No Month Available.*

Mag et al., "Synthesis of Dinucleotides Containing a Bridged Non–Chiral Internucleotide 5'– or 3'–Phosphoramidate Linkage", Tetrahedron, vol. 50, No. 34, pp. 10225–10234, 1994 No Month Available.*

* cited by examiner

*Primary Examiner*—Edna Wong
(74) *Attorney, Agent, or Firm*—Oblon, Spivak, McClelland, Maier & Neustadt, P.C.

(57) ABSTRACT

The invention relates to nucleoside derivatives bearing electrolabile protector groupings and their use in an oligonucleotide synthesis method comprising at least one step of electronic deprotection.

14 Claims, No Drawings

NUCLEOSIDE DERIVATIVES, AND THEIR USE IN OLIGONUCLEOTIDE SYNTHESIS

This is a National Stage Application of PCT/FR97/00770, filed Apr. 30, 1997.

The invention relates to reagents for oligonucleotide synthesis, and in particular to nucleoside derivatives and blocking reagents which can be used for the electrochemical synthesis of oligonucleotides.

Application PCT WO 94/22889 in the name of CIS BIO INTERNATIONAL (inventors TEOULE et al.) describes derivatives of electron conducting polymers (ECP) which can be used as a support for the synthesis of biological polymers, in particular of oligonucleotides. One of the uses of derivatives of electron conducting polymers which is described in this application is the addressed synthesis of oligonucleotides in situ on microelectrodes coated with an electron conducting polymer, which makes it possible, in particular, to obtain oligonucleotide matrices. The oligonucleotide or peptide matrices indeed constitute a very advantageous tool in the sequencing field, as well as in the diagnostic field (genetic diseases, infectious diseases, cancer, cell typing) or for the screening of active molecules.

During conventional methods of oligonucleotide synthesis on a solid support, nucleotides are used whose phosphate group, the exocyclic amine function of the A, C and G bases, and the 5'-OH group of the sugar bear protecting groups. To carry out each step for extending the oligonucleotide chain, the 5'-OH group of the sugar in the nucleoside from which the extension proceeds is deprotected so that the 5'-OH function liberated can react, in the presence of a coupling agent, with the phosphate group of the next nucleotide in order to form a phosphotriester bond (optionally via a phosphite which is then converted to a phosphotriester by oxidation). The cycle is then repeated: deprotection of the 5'-OH group/coupling of the next nucleotide via a phosphotriester bond, until the oligonucleotide of the desired size is obtained. At the end of each cycle, the unreacted 5'-OH functions are blocked by esterification; this step is called <<capping>>.

The protection of the A, C and G bases is designed to avoid spurious reactions involving the exocyclic amine functions of these bases. The protecting groups for these bases, as well as those for the phosphate group, are cleaved at the end of the oligonucleotide synthesis.

The use of an electron conducting polymer as a synthesis support makes it possible to carry out the synthesis of oligonucleotides using one or more steps for electrochemical cleavage of the different protecting groups. This electrochemical deprotection is achieved by creating a potential difference between the working electrode and a counter-electrode.

The use of microelectrodes arranged in the form of a matrix as a solid support for the in situ synthesis of oligonucleotides makes it possible to carry out, for the addition of a given nucleotide, the selective electrochemical deprotection of the 5'-OH function of the developing oligonucleotide chains on some of the electrodes of the matrix; this therefore makes it possible to add the relevant nucleotide only to the desired oligonucleotide chains and to obtain, at the end of the synthesis, oligonucleotide matrices bearing, at different points, oligonucleotides of different sequences.

Application PCT WO 94/22889 cited above, thus describes the use of a thiopixyl group or of a p-nitrobenzoyl group as electrolabile protecting group for the 5'-OH function of the sugar.

In order to be in a position to synthesize oligonucleotides with a variety of sequences using one or more electrochemical deprotection steps, it is advisable to use, for all the functions to be protected, mutually compatible protecting groups.

Accordingly, it should be possible for the electrolabile protecting group for the 5'-OH function of the sugar to be cleaved at a voltage which does not affect either the stability of the nucleosides or that of the protecting groups for the exocyclic amine function of the A, C and G bases. As regards the latter, they should not modify the electronic properties of the base, which would risk influencing its reactivity or the stability of the N-glycoside bond. Protecting groups should therefore be selected which do not destabilize the nucleosides in relation to the reagents for oligonucleotide synthesis, or in relation to reactive species generated during the application of the deprotection voltage, and which, in addition, allow sufficient solubility of the nucleoside.

Likewise, the protecting group for the phosphorus in 3' should be stable under the conditions used for the electrochemical deprotection of the sugar and of the bases.

Finally, the ester formed during the capping in order to block the unreacted 5'-OH functions should Ad 11also be stable under these conditions.

The inventors have now developed nucleoside derivatives bearing protecting groups which satisfy all the above-mentioned conditions, and in particular which make it possible to easily carry out an electrochemical deprotection during the synthesis of oligonucleotides. The subject of the present invention is the use, in a method for the synthesis of oligonucleotides comprising at least one electrochemical step, of at least one nucleoside derivative corresponding to the formula (I) below:

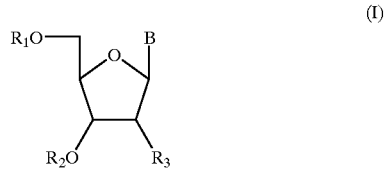

(I)

in which $R_1$ represents:

an electrolabile group corresponding to the following formula (IIa):

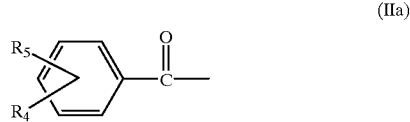

(IIa)

in which $R_4$ represents an $NO_2$ group and $R_5$ represents a hydrogen atom, a linear or branched linear or branched $C_1$ to $C_{10}$ alkyl group, a group

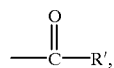

or a group

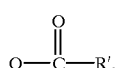

where R' represents a linear or branched $C_1$ to $C_{10}$ alkyl group, or a group —O—R' where R' represents a $C_1$ to $C_{10}$ alkyl group, or alternatively an electrolabile group corresponding to the following formula (IIb):

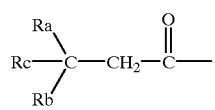

(IIb)

in which one of the groups Ra, Rb or Rc represents a phenyl group, or a substituted phenyl group, and the other two represent hydrogen atoms, $R_2$ represents a hydrogen atom, or a phosphoramidite, phosphonate or phosphotriester group;

$R_3$ represents a hydrogen atom, a hydroxyl radical, a substituted hydroxyl radical or a halogen.

B represents a radical derived from a purine or a pyrimidine base corresponding to one of the following formulae:

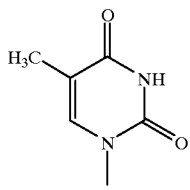

(III)

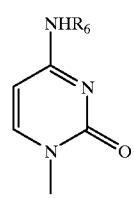

(IV)

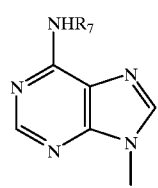

(V)

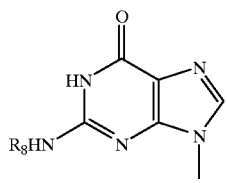

(VI)

where $R_6$ represents a protecting group for the amine function, other than as isobutyryl or phenylpropionyl group, corresponding to one of the formulae (VII), (VIII) and (IX) below:

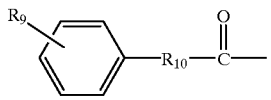

(VII)

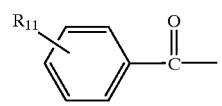

(VIII)

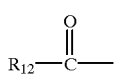

(IX)

in which $R_9$ and $R_{11}$, which may be identical or different, represent a hydrogen atom, or a $C_1$–$C_{10}$ alkoxy or alkyl group, $R_{12}$ represents a linear or branched $C_1$–$C_{10}$ alkyl radical, and $R_{10}$ is chosen from the radicals of formula:

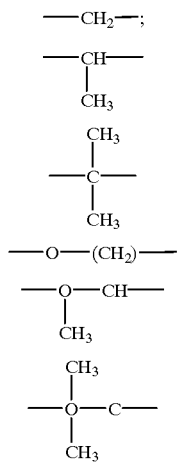

$R_7$ represents a protecting group for the amine function, other than a phenylpropionyl group, corresponding to one of the formulae (VII), (VIII) and (IX) defined above;

$R_8$ represents a protecting group for the amine function, other than an isobutyryl, phenylpropionyl or phenoxyacetyl group, corresponding to one of the formulae (VII), (VIII) and (IX) defined above;

with the exception of the derivatives in which $R_1$ is an electrolabile group of formula (IIa) in which $R_4$ represents an $NO_2$ group and $R_5$ a hydrogen atom, and B represents thymine.

Preferred derivatives are those in which $R_1$ corresponds to the formula (IIa), in which $R_4$ represents an $NO_2$ group and $R_5$ represents a hydrogen atom, and among these, derivatives in which:

B corresponds to the formula IV in which $R_6$ is an anisoyl group, or alternatively B corresponds to the formula V in which $R_7$ is a benzoyl group or a phenoxyacetyl group, or alternatively B corresponds to the formula VI in which $R_8$ is a t-butylphenoxyacetyl group.

The abovementioned nucleoside derivatives can undergo, without alteration, all the oligonucleotide synthesis operations, and in particular the application of the electric voltage necessary for cleaving the electrolabile protecting groups.

They are therefore particularly appropriate for use for the synthesis of oligonucleotides on supports coated with electron conducting polymers, in particular microelectrodes, or microelectrode matrices.

It is also possible, in the same manner, to use the nucleoside derivatives for the synthesis of structural analogs of nucleic acids (antisense, PNA and the like).

The invention also covers new nucleoside derivatives which can be used for the synthesis of oligonucleotides in accordance with the invention. They are the derivatives of general formula (I) as defined above, with the exception of the derivative in which:

$R_1$ is an electrolabile group of formula (IIa) in which $R_4$ represents an $NO_2$ group and $R_5$ a hydrogen atom, and B corresponds to the formula (III), and of the derivative in which:

$R_1$ is an electrolabile group of formula (IIa) in which $R_4$ represents an $NO_2$ group and $R_5$ a hydrogen atom, and B corresponds to the formula (IV) in which $R_6$ is a benzoyl group.

The subject of the present invention is also a method of oligonucleotide synthesis by successive addition of nucleotides starting with a first nucleoside attached to a solid support, each addition of a nucleotide comprising the deprotection of the 5'-OH function of the nucleotide or of the preceding nucleoside, and the coupling of the nucleotide to be added, to the said deprotected 5'-OH function, in which method at least one of the steps of addition of a nucleotide is carried out using, in accordance with the invention, a nucleoside derivative as defined above, and an electrochemical deprotection of the 5'-OH function of the said nucleoside derivative is carried out.

According to a preferred embodiment of the method in accordance with the invention, the solid support consists of at least one electrode coated with an electron conducting polymer; advantageously, it is a copolymer of a nucleoside derivative and an electron conducting polymer such as those defined in application PCT WO 94/22889.

Advantageously, the solid support consists of several juxtaposed electrodes, and, if desired, the electrochemical deprotection of the 5'-OH function preceding the coupling of a given nucleotide is carried out only on some of these electrodes.

According to another preferred embodiment of the method in accordance with the invention, the electrochemical deprotection of the 5'-OH function is carried out by applying to the electrode bearing the solid support for synthesis a potential difference of between –1.6 V and –0.7 V relative to an Ag/AgNO3 reference electrode.

According to another embodiment of the method in accordance with the invention, a capping treatment with isobutyric anhydride is carried out after each step of coupling of a nucleotide in order to block the 5'-OH functions which have not reacted at the end of the coupling step. The use of isobutyric anhydride allows the formation of a stable ester under the conditions for deprotection of the 5'-OH function.

The present invention will be understood more clearly with the aid of the additional description which follows, which refers to exemplary embodiments of the method in accordance with the invention.

It should be clearly understood, however, that these examples are given solely by way of illustration of the subject of the invention and do not in any manner constitute a limitation thereto.

EXAMPLE 1

Preparation of the Deoxycytidine Derivative

1. Choice of the Functional Protections

Preliminary solubility tests made it possible to eliminate the isobutyryl group, for the protection of the amine function in deoxycytidine, because of the poor solubility of 5'-p-nitrobenzoyl-4-N-isobutyryl-deoxycytidine in organic solvents. The phenylpropionyl group is advantageous because the 5'-p-nitrobenzoyl-4-N-phenylpropionyldeoxycytidine is very soluble in organic solvents. The anisoyl group also confers on the 5'-nitrobenzoylated derivative of deoxycytidine a better solubility than the benzoyl group.

As synthesis tests with electrochemical deprotection did not give good results as regards N-phenylpropionyl deoxycytidine, the stability of the nucleoside protected with N-anisoyl deoxycytidine was checked. The nucleosides were dissolved in 0.1 M tetra-butylammonium perchlorate in methanol. They were subjected to a voltage of –1.35 V for 30 minutes. Analysis of the reaction mixture showed that the cleavage of the phenylpropionyl group is complete under these conditions. The anisoyl group, for its part, is not cleaved. It was therefore decided to replace N-phenylpropionyldeoxycytidine with N-anisoyldeoxycytidine and to prepare the corresponding phosphoramidite for the synthesis in situ.

2. Synthesis of the Nucleoside

The synthesis of 5'-p-nitrobenzoyl-4-N-anisoyldeoxycytidine was carried out by reacting p-nitrobenzoyl chloride (1.1 eq) with 4-N-anisoyldeoxycytidine (1 eq) in pyridine. After extraction with a dichloromethane/sodium bicarbonate mixture, the product was obtained by chromatography on a silica column. The elution is carried out with 4% ethanol in dichloromethane. This nucleoside is fairly soluble in organic solvents.

3. Preparation of the Amidite of Deoxycitidine

The nucleoside (1 eq) is dried in a dichloromethane/acetonitrile mixture and reacted with 1.2 eq of bisdiisopropylaminocyanoethoxyphosphine and 0.5 eq of diisopropylammonium tetrazolide in anhydrous dichloromethane. After reacting for 2 hours, the reaction mixture is diluted and washed successively with 0.5 M sodium bicarbonate and saturated sodium chloride. The organic phase is evaporated to dryness. After redissolution in chloroform, the product is precipitated in hexane, dried under vacuum and stored under argon. This amidite is soluble in acetonitrile, a solvent in which oligonucleotide syntheses are conventionally carried out.

EXAMPLE 2

Preparation of the Deoxyadenosine Derivative

1) Choice of the Functional Protections

The two deoxyadenosine derivatives normally used in oligonucleotide synthesis, namely the benzoylated derivative (normally, deprotection 16 hours at 55° C.), and the phenoxyacetylated derivative (normally, deprotection 16 hours at room temperature or 4 hours at 55° C.) were prepared.

2) Synthesis of 5'-O-p-Nitrobenzoyl-6-N-Benzoyl Deoxyadenosine

The synthesis of this product is carried out by reacting 1 eq of p-nitrobenzoyl chloride with 6-N-benzoyldeoxyadenosine for 4 hours in pyridine. After hydrolysis of the excess reagent, partial evaporation of the pyridine, extraction and evaporation of the chloroformic phase, the product is obtained by column chromatography (elution 4% methanol).

3) Synthesis of 5'-O-p-Nitrobenzoyl-6-N-Phenoxyacetyldeoxyadenosine

The synthesis of this product is carried out by reacting 1.1 eq of p-nitrobenzoyl chloride with 6-N-phenoxyacetyldeoxyadenosine for 4 hours in pyridine. After hydrolysis of the excess reagent, almost complete evaporation of the pyridine, and ethyl acetate/sodium bicarbonate extraction, the ethyl acetate phase is evaporated to dryness. The product is obtained by column chromatography with a gradient of methanol in chloroform (elution 4% methanol).

4) Result

The two derivatives exhibit an appropriate solubility. The phenoxyacetylated nucleoside will be chosen because of its more favorable electrochemical deprotection conditions.

5) Preparation of the Amidite of Deoxyadenosine

5'-O-p-Nitrobenzoyl-6-N-phenoxyacetyldeoxyadenosine (1 eq) is dried in a dichloromethane/acetonitrile mixture and reacted with 1.2 eq of bisdiisopropylaminocyanoethoxyphosphine and 0.5 eq of diisopropylammonium tetrazolide in anhydrous dichloromethane. After reacting for 2 hours, the reaction mixture is diluted and washed successively with 0.5 M sodium bicarbonate and saturated sodium chloride. The organic phase is evaporated to dryness. After precipitation in hexane, the product is dried under vacuum and stored under argon. This amidite is soluble in acetonitrile, a solvent in which oligonucleotide syntheses are conventionally carried out.

EXAMPLE 3

Preparation of the Deoxyguanosine Derivative

1) Choice of the Protecting Group

Tests for protecting deoxyguanosine on its amine function at the 2-position were carried out with the following groups: isobutyryl, phenoxyacetyl and t-butylphenoxyacetyl.

2) Synthesis of 5'-O-p-Nitrobenzoyl-2-N-Isobutyryldeoxyguanosine

The synthesis of this product is carried out by reacting 1.1 eq of p-nitrobenzoyl chloride with 2-N-isobutyryldeoxyguanosine for 16 hours in pyridine. After extraction with a dichloromethane/sodium bicarbonate mixture and evaporation to dryness, the product is taken up in chloroform. This product was not used because it was too insoluble.

3) Synthesis of 5'-O-p-Nitrobenzoyl-2-N-Phenoxyacetyldeoxyguanosine

The synthesis of this product is carried out by reacting 1.1 eq of p-nitrobenzoyl chloride with 2-N-phenoxyacetyldeoxyguanosine for 16 hours in pyridine. After extraction with a dichloromethane/sodium bicarbonate mixture and evaporation to dryness, the product is taken up in chloroform and purified on a silica column (elution 4% methanol). The product is only slightly soluble in organic solvents.

4) Synthesis of the Amidite of 5'-O-p-Nitrobenzoyl-2-N-Phenoxyacetyldeoxyguanosine The nucleoside is dried by coevaporation in a dichloromethane/acetonitrile mixture and reacted with 1.2 eq of bisdiisopropylaminocyanoethoxyphosphine and 0.5 eq of diisopropylammonium tetrazolide in anhydrous dichloromethane (product which is not soluble). After reacting for 2 hours, the reaction mixture is diluted and washed successively with 0.5 M sodium bicarbonate and saturated sodium chloride. The organic phase is evaporated to dryness. After precipitation in hexane, the product is dried under vacuum and stored under argon. The amidite is soluble in dichloromethane. It is hardly soluble in acetonitrile and a deposit is observed in the flask after less than one hour. A more soluble derivative was prepared by substituting the phenoxyacetyl group.

5) Synthesis of 2-N-t-Butylphenoxyacetyldeoxyguanosine

The synthesis of this product required the preparation of t-butylphenoxyacetyl chloride from sodium t-butylphenoxide and ethyl chloroacetate. The ethyl t-butylphenoxyacetate obtained is cleaved with potassium hydroxide in order to liberate the t-butylphenoxyacetic acid. The acid chloride is obtained by heating this acid in thionyl chloride. After removing the excess thionyl chloride, the t-butylphenoxyacetyl chloride is reacted with deoxyguanosine according to the procedure described by SCHULHOF et al. for 2-N-phenoxyacetyldeoxyguanosine [Nucleic Acids Res., 15(2), p. 397–415, (1987)].

6) Synthesis of 5'-O-p-Nitrobenzoyl-2-N-t-Butylphenoxyacetyldeoxyguanosine

The synthesis of this product is carried out by reacting 1.1 eq of p-nitrobenzoyl chloride with 2-N-t-butylphenoxyacetyldeoxyguanosine for 16 hours in pyridine. After extraction with a dichloromethane/methanol mixture and evaporation to dryness, the product is taken up in chloroform/hexane (8/2) and purified on a silica column (elution 3% methanol). The product obtained is very soluble in organic solvents.

7) Result

Since the usual derivatives of deoxyguanosine were not sufficiently soluble, it was necessary to use the t-butylphenoxyacetic group. This group made it possible to prepare a very soluble deoxyguanosine derivative, it too bearing a protecting group which is cleaved under gentle conditions.

8) Preparation of the Amidite of Deoxyguanosine

5'-O-p-nitrobenzoyl-2-N-t-butylphenoxyacetyldeoxyguanosine (1 eq) is dried in a dichloromethane/acetonitrile mixture and reacted with 1.2 eq of bisdiisopropylaminocyanoethoxyphosphine and 0.5 eq of diisopropylammoniumtetrazolide in anhydrous dichloromethane. After reacting for 2 hours, the reaction mixture is diluted and washed successively with 0.5 M sodium bicarbonate and saturated sodium chloride. The organic phase is evaporated to dryness. After redissolution in chloroform and precipitation in hexane, the product is dried under vacuum and stored under argon. This amidite is soluble in acetonitrile, a solvent in which oligonucleotide syntheses are conventionally carried out.

EXAMPLE 4

Preparation of the Cleavable Graft Support

1) Principle

The graft support was prepared by copolymerization of pyrrole and of nucleoside pyrrole. In order to be able to analyze the oligonucleotide formed, the nucleoside and the pyrrole are linked via an ester function which will be cleaved with aqueous ammonia during the deprotection of the oligonucleotide. The nucleoside is protected in 5' with a p-nitrobenzoyl, which is stable under the conditions used for the polymerization, in order to allow blocking of the support before synthesis.

2) Preparation of the Succinyl Nucleoside p-Nitrobenzoylthymidine (10 mmol) is dried by coevaporation in pyridine. It is taken up in 10 ml of pyridine and succinic anhydride (12 mmol) and DMAP (12 mmol) are added. The reaction is carried out for 16 hours at room temperature. After dichloromethane/sodium bicarbonate extraction, the reaction mixture is evaporated to dryness, taken up in dichloromethane and then purified on a silica column.

3) Preparation of the Nucleoside Pyrrole

The succinylated 5'-p-nitrobenzoylthymidine (2 mmol) is dried by coevaporation in anhydrous pyridine and taken up in 20 ml of acetonitrile. Dicyclohexylcarbodiimide (2.2 mmol) and aminoethylpyrrole (2 mmol) are added. The reaction is carried out for 16 hours. The DCU (dicyclohexylurea) precipitate is removed by filtration. The reaction mixture is evaporated and taken up in 100 ml of dichloromethane. After extraction with dichloromethane/sodium bicarbonate, and evaporation of the organic phase, the product is obtained by chromatography on a silica column with a gradient of methanol in chloroform.

4) Copolymerization with Pyrrole

The nucleoside coupled to pyrrole, $10^{-3}$ M, and the pyrrole $10^{-2}$ M, are copolymerized in solution in 0.1 M tetrabutylammonium perchlorate in acetonitrile. The synthesis is carried out by sweeping between −0.35 V and +0.85 V relative to $Ag/AgNO_3$. The electrochemical cell is composed of a polypropylene tube in which an electrode and a counter-electrode, both consisting of a 0.3×1 cm platinum ribbon and a reference electrode ($Ag/AgNO_3$), are dipped. During the sweeping, the pyrrole copolymer is deposited in the form of an adherent black film on the electrode.

The support thus obtained can be used for the synthesis of oligonucleotides with electrochemical deprotection when it is desired to recover the oligonucleotide for analytical purposes at the end of the synthesis.

EXAMPLE 5

Synthesis in situ on a Cleavable Support of the Oligonucleotide AAAAT

The first nucleoside in 3' was introduced during the copolymerization which served to prepare the support: it is a thymidine protected with a p-nitrobenzoyl on its hydroxyl in 5'. This first nucleoside is deprotected for 15 minutes at −1.35 V in 0.1 M $Bu_4N^+ClO_4^-$ in methanol. The electrode is disconnected and placed in a synthesis column. The following step of the cycle are then carried out (condensation, blocking, oxidation on the synthesizer). The condensation is performed with the amidite A protected with a p-nitrobenzoyl on its hydroxyl function in 5' and a phenoxyacetyl group on the amine function of the nucleic base. The phosphite is oxidized with an iodine solution. For the blocking of the unreacted 5'-OH functions, 10% isobutyric anhydride in THF is used with a contact time of 30 seconds. Indeed, acetic anhydride is not suitable for the blocking because the ester formed is cleaved during the electrochemical deprotection.

The electrode is taken out of the column and placed in the electrochemical cell. The p-nitrobenzoyl group is cleaved by application of a voltage of −1.35 V for 15 minutes. The electrode is disconnected and then replaced in the synthesis column. The chemical steps are then carried out: condensation with the amidite A, blocking and oxidation. This cycle alternating an electrochemical deprotection step and three chemical steps is continued by introducing again three times the amidate A until AAAAT bearing protected amine functions is obtained.

At the end of the synthesis, the oligonucleotide obtained is cleaved from the support and the protecting groups for the amine functions are cleaved by heating in aqueous ammonia for 16 hours.

EXAMPLE 6

Synthesis in situ on a Cleavable Support of the Oligonucleotide CCCCT

The synthesis is carried out according to the procedure described for AAAAT by replacing, in each cycle, the amidite of 5'-p-nitrobenzoyl-N-phenoxyacetyldeoxyadenosine with that of 5'-p-nitrobenzoyl-4-N-anisoyldeoxycytidine.

At the end of the synthesis, the oligonucleotide obtained is cleaved from the support and the protecting groups for the amine functions are cleaved by heating in aqueous ammonia for 16 hours.

EXAMPLE 7

Synthesis in situ on a Cleavable Support of the Oligonucleotide GGGGT

The synthesis is carried out according to the procedure described for AAAAT by replacing, in each cycle, the amidite of 5'-p-nitrobenzyl-N-phenoxyacetyldeoxyadenosine with that of 5'-p-nitrobenzoyl-2-N-t-butylphenoxyacetyldeoxyguanosine.

At the end of the synthesis, the oligonucleotide obtained is cleaved from the support and the protecting groups for the amine functions are cleaved by heating in aqueous ammonia for 16 hours.

EXAMPLE 8

Synthesis in situ on a Cleavable Support of the Oligonucleotide TTTTT

The synthesis is carried out according to the procedure described for AAAAT by replacing, in each cycle, the amidite of 5'-p-nitrobenzyl-N-phenoxyacetyldeoxyadenosine with that of 5'-p-nitrobenzoylthymidine.

At the end of the synthesis, the oligonucleotide obtained is cleaved from the support and the protecting groups for the-amine functions are cleaved by heating for 16 hours in aqueous ammonia.

EXAMPLE 9

Synthesis in situ on a Cleavable Support of the Oligonucleotide TGTCCAGAT

The first nucleoside in 3' was introduced during the copolymerization which served to prepare the support: it is a thymidine protected with a nitrobenzoyl on its hydroxyl in 5'. This first nucleoside is deprotected for 15 minutes at −1.35 V in 0.1 M $Bu_4N^+ClO_4^-$ in methanol. The electrode is disconnected and placed in a synthesis column. The following steps of the cycle are then carried out (condensation, blockage, oxidation on the synthesizer). The condensation is performed with the amidite A protected with a p-nitrobenzoyl on its hydroxyl function in 5' and a phenoxyacetyl group on the amine function of the nucleic base. The oxidation is carried out with an iodine solution. For the blocking of the unreacted 5'-OH functions, 10% isobutyric anhydride in THF is used with a contact time of 30 seconds.

The electrode is taken out of the column and placed in the electrochemical cell. The nitrobenzoyl group is cleaved by application of a voltage of −1.35 V for 15 minutes. The electrode is disconnected and then replaced in the synthesis column. The chemical steps are then carried out: condensation with the amidite A of p-nitrobenzoyldeoxyguanosine, blocking and oxidation. This cycle alternating an electrochemical deprotection step and three chemical steps is continued by introducing successively A,C,C,T,G,T.

At the end of the synthesis, the oligonucleotide obtained is cleaved from the support and the protecting groups for the amine functions are cleaved by heating in aqueous ammonia for 16 hours.

EXAMPLE 10

Preparation of a Noncleavable Graft Support

1) Principle

To carry out the synthesis of the oligonucleotide on the support, it is necessary to introduce onto the matrix a function capable of coupling with a phosphoramidite. This function, which will serve as the point of anchorage for the synthesis in situ of the oligonucleotide, will be advantageously introduced during copolymerization. It is advantageous to introduce a derivative of pyrrole bearing a spacer arm, having at its end a function which is reactive towards the phosphoramidite, this function being protected with an electrolabile group.

In order to be able to keep on the matrix the oligonucleotide formed the first nucleoside and the pyrrole are linked via a phosphodiester function which will therefore be stable during the deprotection of the oligonucleotide with aqueous ammonia. This reagent is protected in order to allow the blocking of the support before synthesis with the p-nitrobenzoyl group which is stable under the conditions used for the polymerization.

2) Nitrobenzoylation of Pyrrole Triethylene Glycol (PYTEG)

PYTEG (10 mmol, 2 g) is dried by coevaporation in anhydrous pyridine. It is taken up in 100 ml of pyridine and nitrobenzoyl chloride (11 ml, 2 g) is added. After reacting for 4 to 16 hours, the solvent is removed and the reaction mixture is taken up in 100 ml of chloroform. The solution is washed with 3×100 ml of saturated $NaHCO_3$. The aqueous phases are counter-extracted with 50 ml of chloroform. The organic phases are combined and evaporated to dryness. The residue is taken up in 5 ml of chloroform and separated on a silica column conditioned in chloroform. The product is eluted with 5% methanol in chloroform. 2.97 g of product are obtained (85% yield).

3. Copolymerization of PYTEG with Pyrrole on an Electrode

PYTEG coupled to nitrobenzoyl, $10^{-3}$ M, and pyrrole, $10^{-2}$ M, were copolymerized in solution in 0.1 M tetrabutylammonium perchlorate in acetonitrile. The synthesis is carried out -by sweeping between −0.35 V and +0.85 V relative to $Ag/AgNO_3$. The electrochemical cell is composed of a polyethylene tube in which an electrode and a counter-electrode, both consisting of a 0.5×1 cm platinum ribbon and a reference electrode ($Ag/AgNO_3$), are dipped. During the sweeping, the copolymer is deposited in the form of an adherent film on the electrode. This support will be used for the synthesis of oligonucleotides with electrochemical deprotection when it is not desired to cleave the oligonucleotide at the end of the synthesis.

What is claimed is:

1. A method of oligonucleotide synthesis, comprising:

successive adding nucleotides starting with a first nucleoside attached to a solid support, wherein each addition of a nucleotide comprises the cleavage of the protecting group for the 5'-OH function of the nucleotide or of the preceding nucleoside, and the coupling of the nucleotide to be added, to the deprotected 5'-OH function, wherein at least one of addition of a nucleotide is carried out with a nucleoside derivative represents by the formula (I), and wherein the cleavage of the protecting group for the 5'-OH function of the nucleotide represented by formula (I) is carried out by an electrochemical reaction,

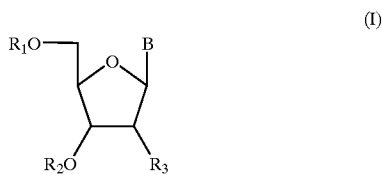

wherein
$R_1$ represents:
an electrolabile group represented by formula (IIa):

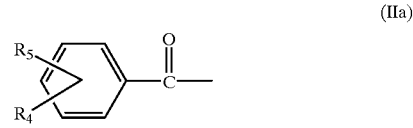

in which $R_4$ represents an $NO_2$ group and $R_5$ represents a hydrogen atom, a linear or branch $C_1$ to $C_{10}$ alkyl group, a group

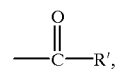

or a group

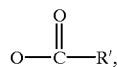

where R' represents a linear or branched $C_1$ to $C_{10}$ alkyl group, or a group —O—R' where R' represents a linear or branched $C_1$ to $C_{10}$ alkyl group, or alternatively an electrolabile group represented by formula (IIb):

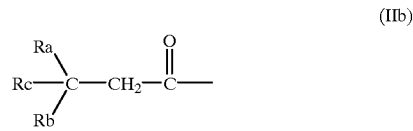

in which one of the groups Ra, Rb or Rc represents a phenyl group, or a substituted phenyl group, and the other two represent hydrogen atoms, $R_2$ represents a hydrogen atom, or a phosphoramidite, phosphonate or phosphotriester group;

$R_3$ represents a hydrogen atom, a hydroxyl radical, a substituted hydroxyl radical or a halogen, B represents a radical derived from a purine or a pyrimidine base represented by one of the following formulae:

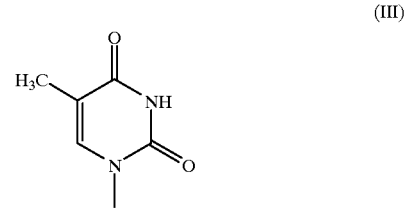

-continued

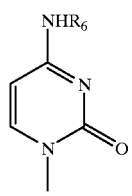
(IV)

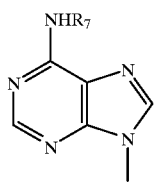
(V)

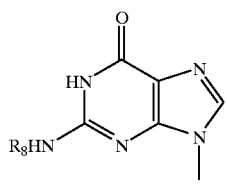
(VI)

wherein $R_6$ represents a protecting group for the amine function, other than an isobutyryl or phenylpropionyl group, represented by one of the formulae (VII), (VIII) or (IX) below:

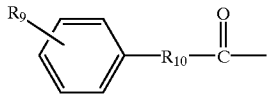
(VII)

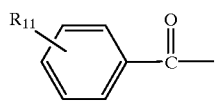
(VIII)

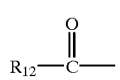
(IX)

in which $R_9$ and $R_{11}$, which may be identical or different, represent a hydrogen atom, or a $C_1$–$C_{10}$ alkoxy or alkyl group, $R_{12}$ represents a linear or branched $C_1$–$C_{10}$ alkyl radical, and $R_{10}$ is represented by the formula:

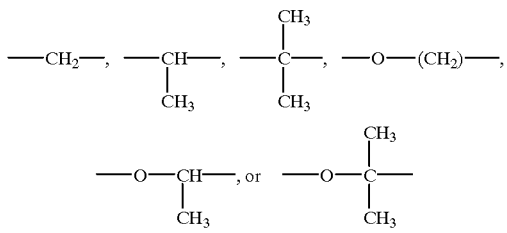

$R_7$ represents a protecting group for the amine function, other than a phenylpropionyl group, represented by one of the formulae (VII), (VIII) or (IX) defined above;
$R_8$ represents a protecting group for the amine function, other than an isobutyryl, phenylpropionyl or phenoxy- acetyl group, corresponding to one of the formulae (VII), (VIII) or (IX) defined above;

with the exception of the derivatives in which $R_1$ is an electrolabile group represented by formula (IIa) in which $R_4$ represents an $NO_2$ group and $R_5$ a hydrogen atom, and B is represented by formula (III).

2. The method as claimed in claim 1, wherein the solid support consists of at least one electrode coated with an electron conducting polymer.

3. The method as claimed in claim 2, wherein the electrochemical deprotection of the 5'-OH function is carried out by applying to the electrode bearing the solid support for synthesis a voltage difference of between −1.6 V and −0.7 V relative to an $Ag/AgNO_3$ reference electrode.

4. The method as claimed in claim 1, wherein the solid support consists of several juxtaposed electrodes, it being possible for the electrochemical deprotection of the 5'-OH function, optionally, to be carried out only on some of these electrodes.

5. The method as claimed in claim 1, wherein after each step of coupling a nucleotide, a treatment is carried out with isobutyric anhydride.

6. The method as claimed in claim 1, wherein $R_1$ is represented by formula (IIa), and wherein $R_4$ represents an $NO_2$ group and $R_5$ represents a hydrogen atom.

7. The method as claimed in claim 1, wherein B is represented by formula (IV) and wherein $R_6$ is an anisoyl group.

8. The method as claimed in claim 1, wherein B is represented by formula (V) and wherein $R_7$ is a benzoyl group or a phenoxyacetyl group.

9. The method as claimed in claim 1, wherein B is represented by (VI), and wherein $R_8$ is a t-butylphenoxyacetyl group.

10. A nucleoside derivative represented by formula (I):

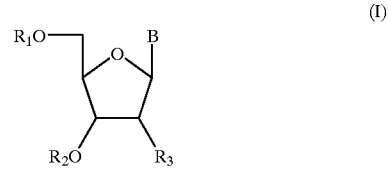
(I)

wherein
$R_1$ represents:
an electrolabile group represented by formula (IIa):

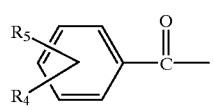
(IIa)

in which $R_4$ represents an $NO_2$ group and $R_5$ represents a hydrogen atom, a linear or branched $C_1$ to $C_{10}$ alkyl group, a group

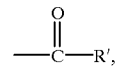

or a group

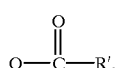

where R' represents a linear or branched $C_1$ to $C_{10}$ alkyl group, or a group —O—R' where R' represents a linear or branched $C_1$ to $C_{10}$ alkyl group, or alternatively an electrolabile group represented by formula (IIb):

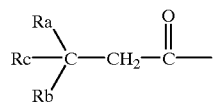

(IIb)

in which one of the groups Ra, Rb or Rc represents a phenyl group, or a substituted phenyl group, and the other two represent hydrogen atoms, $R_2$ represents a hydrogen atom, or a phosphoramidite, phosphonate or phosphotriester group;

$R_3$ represents a hydrogen atom, a hydroxyl radical, a substituted hydroxyl radical or a halogen, B represents a radical derived from a purine or a pyrimidine base represented by one of the following formulae:

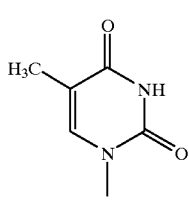

(III)

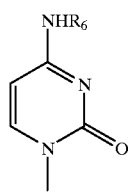

(IV)

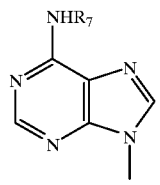

(V)

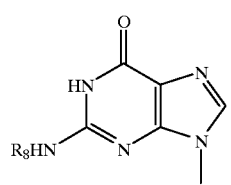

(VI)

wherein $R_6$ represents a protecting group for the amine function, other than an isobutyryl or phenylpropionyl group, represented by one of the formulae (VII), (VIII) or (IX) below:

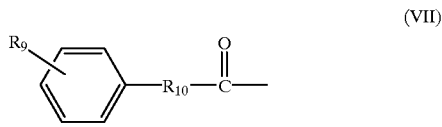

(VII)

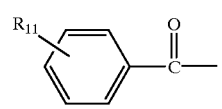

(VIII)

(IX)

in which $R_9$ and $R_{11}$, which may be identical or different, represent a hydrogen atom, or a $C_1$–$C_{10}$ alkoxy or alkyl group, $R_{12}$ represents a linear or branched $C_1C_{10}$ alkyl radical, and $R_{10}$ is represented by the formula:

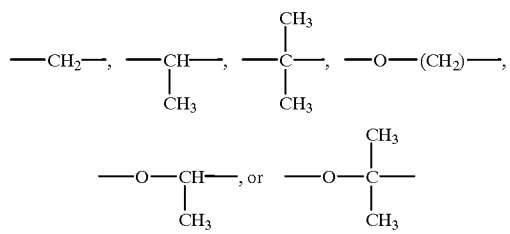

$R_7$ represents a protecting group for the amine function, other than a phenylpropionyl group, represented by one of the formulae (VII), (VIII) or (IX) defined above;

$R_8$ represents a protecting group for the amine function, other than an isobutyryl, phenylpropionyl or phenoxyacetyl group, corresponding to one of the formulae (VII), (VIII) or (IX) defined above;

with the exception of the derivatives in which $R_1$ is an electrolabile group of formula (IIa) in which $R_4$ represents an $NO_2$ group and $R_5$ a hydrogen atom, and B corresponds either to the formula (III), or to the formula (IV) in which $R_6$ is a benzoyl group.

11. The nucleoside derivative as claimed in claim 10, wherein $R_1$ is represented by formula (IIa), and wherein $R_4$ represents an $NO_2$ group and $R_5$ represents a hydrogen atom.

12. The nucleoside derivative as claimed in claim 10, wherein B is represented by formula (IV) and wherein $R_6$ is an anisoyl group.

13. The nucleoside derivative as claimed in claim 10, wherein B is represented by formula (V) and wherein $R_7$ is a benzoyl group or a phenoxyacetyl group.

14. The nucleoside derivative as claimed in claim 10, wherein B is represented by (VI), and wherein $R_8$ is a t-butylphenoxyacetyl group.

* * * * *

UNITED STATES PATENT AND TRADEMARK OFFICE
CERTIFICATE OF CORRECTION

PATENT NO. : 6,187,914
DATED : February 13, 2001
INVENTOR(S) : TEOULE et al

Page 1 of 1

It is certified that error appears in the above-identified patent and that said Letters Patent is hereby corrected as shown below:

On the title page, Item (30), the Foreign Application Priority Date is incorrectly listed. Item (30) should read as follows:

(30) Foreign Application Priority Data

May 3, 1996   (FR)........................ 96 05553

Signed and Sealed this

Fifth Day of June, 2001

*Attest:*

*Attesting Officer*

NICHOLAS P. GODICI

*Acting Director of the United States Patent and Trademark Office*